(12) United States Patent
Bradaric-Baus et al.

(10) Patent No.: US 8,748,668 B2
(45) Date of Patent: Jun. 10, 2014

(54) PHOSPHONIUM SALTS AND METHODS OF THEIR PREPARATION

(75) Inventors: Christine J. Bradaric-Baus, Stony Creek (CA); Yuehui Zhou, Toronto (CA)

(73) Assignee: Cytec Technology Corp., Wilmington, DE (US)

( * ) Notice: Subject to any disclaimer, the term of this patent is extended or adjusted under 35 U.S.C. 154(b) by 73 days.

(21) Appl. No.: 12/899,097

(22) Filed: Oct. 6, 2010

(65) Prior Publication Data

US 2011/0021838 A1 Jan. 27, 2011

Related U.S. Application Data

(62) Division of application No. 10/549,223, filed as application No. PCT/US2004/006961 on Mar. 8, 2004, now Pat. No. 7,829,744.

(30) Foreign Application Priority Data

Mar. 31, 2003 (CA) .................................. 2424215

(51) Int. Cl.
C07F 9/40 (2006.01)
(52) U.S. Cl.
USPC ............................................... 568/10; 568/9
(58) Field of Classification Search
USPC ............ 429/200, 199, 188; 568/9, 10; 514/75
See application file for complete search history.

(56) References Cited

U.S. PATENT DOCUMENTS

| | | | |
|---|---|---|---|
| 3,976,566 | A | 8/1976 | Petrovich |
| 4,017,610 | A | 4/1977 | Baker |
| 4,837,394 | A | 6/1989 | Alexandrovich et al. |
| 4,867,790 | A | 9/1989 | Jochum et al. |
| 2004/0106823 | A1 | 6/2004 | Roberstson et al. |

FOREIGN PATENT DOCUMENTS

| | | | | |
|---|---|---|---|---|
| EP | 029003 | | 10/1980 | |
| EP | 0149480 | | 1/1985 | |
| EP | 0161128 | | 11/1985 | |
| EP | 0455257 | | 11/1991 | |
| EP | 0640646 | | 3/1995 | |
| EP | 0675130 | | 10/1995 | |
| EP | 0895997 | | 1/1999 | |
| EP | 1182197 | | 8/2000 | |
| JP | 63119490 | | 5/1988 | |
| JP | 11172577 | | 6/1999 | |
| JP | 2001164461 | | 6/2001 | |
| WO | 9723490 | | 7/1997 | |
| WO | 0016902 | | 3/2000 | |
| WO | WO00/16902 | A1 * | 3/2000 | .............. B01J 31/02 |
| WO | 01-87900 | | 11/2001 | |
| WO | WO01/87900 | A1 * | 11/2001 | .............. C07F 9/54 |
| WO | WO02/079212 | A1 * | 10/2002 | .............. C07F 9/54 |
| WO | 03-020843 | | 3/2003 | |
| WO | 03051894 | | 6/2003 | |

OTHER PUBLICATIONS

Welton, Chem. Rev. 99, pp. 2071-2083 (1999).
Kanazawa, Antimicrobial Agents and Chemotherapy, v. 38(5) pp. 945-952 (1994).
Hays, H., J. Org. Chem., 1966, v. 31(11), pp. 3817-3820.
Kanazawa, J. Polymer Sci., v. 31(6), pp. 1441-1447 (1993).
Ludley, P. et al. Tetrahedron Letters v. 42, No. 10, Mar. 4, 2001, pp. 2011-2014.
Comyns, C. et al., Catalysis Letters, v. 67, No. 2-4, Mar. 10, 2000, pp. 113-115.
Karodia, N. et al., Chemical Communications, No. 21, 1998, pp. 2341-2342.
Abdallah, D.J. et al., J. Amer. Chem. Soc., v. 122(13), Apr. 5, 2000, pp. 3053-3062.
Esteruelas, M.A. et al., Organometallics, v. 16(21) Oct. 14, 1997, pp. 4572-4580.
Imrie, C. et al., J. Organic Chemistry, v. 58(21), 1993, pp. 5643-5649.
Dema, A. et al., Organometallics, v. 10(4) 1991, pp. 1197-1200.
Jones, R.A. et al., J. Chem. Soc., Perkin Transactions II, No. 1, 1980, pp. 117-120.
Cerichelli, G. et al., Langmuir, v. 16(1) Jan. 11, 2000, pp. 156-171.
Albanese, D. et al., Tetrahedron Letters, v. 36(48), pp. 8865-8866.
Ogata, M. et al., J. of Applied Polymer Sci., v. 48(4), Apr. 20, 1993, pp. 583-601.

(Continued)

Primary Examiner — Johann R Richter
Assistant Examiner — Pancham Bakshi
(74) Attorney, Agent, or Firm — Charles E. Bell

(57) ABSTRACT

Methods for preparing phosphonium salts by reacting a primary phosphine or a secondary phosphine with an ester compound selected from the group consisting of: a phosphate triester; a phosphonate diester; a sulfate diester; and a sulfonate ester; to form a phosphonium salt of formula VII

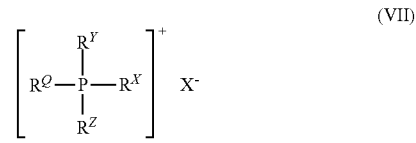

(VII)

wherein each of $R^Q$, $R^X$, $R^Y$, and $R^Z$ is independently hydrocarbyl and $X^-$ is a phosphate, phosphonate, sulfate, or sulfonate are provided herein. These phosphonium salts may find utility in a wide range of applications, including as surfactants, as polar solvents (ionic liquids), as antimicrobial agents, and as a component of spinning finish in polyamide fiber processing.

13 Claims, 2 Drawing Sheets

(56) References Cited

OTHER PUBLICATIONS

Adams, C. et al. Chemical Communications, No. 19, 1998, pp. 2097-2098.
Chauvin, Y. et al., Journal of the Chemical Society, Chemical Communications, No. 23, 1990, pp. 1715-1716.
Bohm, V. et al., Chemistry-A European Journal, v. 6(6) Mar. 17, 2000, pp. 1017-1025.
Chauvin, Y. et al., Journal of Catalysis, v. 165, 1997, pp. 275-278.
Fischer, T. et al. Tetrahedron Letters, v. 40(4), Jan. 22, 1999, pp. 793-796.
Wessolowski, H. et al., J. Fluorine Chem., v. 80(2), 1996, pp. 149-152.
Sarbu, T. et al., Maromol. Chem. Phys., 2001, 202, pp. 3379-3397.
Haskin, B.A., et al., J. of Gen. Chem., v. 38(12), 1967, pp. 2652-2658.
Office Action Summary of Oct. 9, 2008 for copending U.S. Appl. No. 10/521,973.
Wasserscheid et al., 2002, CAS: 136:200188.
Holbrey et al., 2002, CAS: 138:338049.
Wasserscheid et al., 2002, CAS: 140:78757.
Office Action Summary of Jun. 17, 2009 for copending U.S. Appl. No. 10/521,973.
Christine J. Bradaric, et al.; "Industrial Preparation of Phosphonium Ionic Liquids," Green Chemistry, 2003, 5, 143-152.
International Search Report for PCT/US2004/006961, date mailed Aug. 5, 2004.
Written Opinion of ISR for PCT/US2004/006961, dated mailed Aug. 5, 2004.
International Preliminary Report on Patentability for PCT/US2004/006961, date completed Aug. 18, 2005.
Oliver, H., Nanaqueous Ionic Liquids (NAILS): Aqueous Phase Organometallic Catalysis, Concepts and Applications, May 28, 1998, pp. 555-563.
Yanmaele, L., Research Disclosure, No. 287, 1988, pp. 133-134.
Barraud, A. et al., Langmuir-Blodgett Film, v. 160(1), Jun. 1, 1988, pp. 81-85.
Chauvin, V. et al., Catalytic Dimerization of Olefins by Nickle Complexes in Organochloroaluminate Molten Salts, v. 99(17), 1990, pp. 822-832.
Opposition paper for EP1387813, dated Mar. 4, 2008.
International Search Report for PCT/CA03/01189, mailed Jan. 2, 2004.
International Preliminary Examination Report for PCT/CA03/01189, completed Sep. 30, 2004.

* cited by examiner

PHOSPHONIUM SALTS AND METHODS OF THEIR PREPARATION

CROSS-REFERENCE TO RELATED APPLICATIONS

This application is a divisional application of U.S. patent application Ser. No. 10/549,223, filed Feb. 8, 2007 (allowed), which is the U.S. National Phase application of International Application No. PCT/US2004/006961, filed Mar. 8, 2004, which claims benefit of priority from Canadian Patent Application No. 2,424,215, filed Mar. 31, 2003, each of which is incorporated herein by reference in its entirety.

FIELD OF THE INVENTION

The present invention relates to phosphonium salts and their methods of preparation.

BACKGROUND OF THE INVENTION

Phosphonium salts may be used in a wide range of applications, including: as surfactants; as a component in spinning finish agents for aromatic polyamide fibers (JP11172577 A2, published Jun. 29, 1999); as antimicrobial agents (Kanazawa et al. (1994) *Antimicrobial Agents and Chemotherapy*, vol. 38(5), p. 945-952); and as polar solvents known as "ionic liquids" (for a recent review, see Thomas Welton (Chem. Rev. 1999, 99, 2071-2083)).

For many purposes, a phosphonium salt having a non-halide anion is desirable. Phosphonium non-halide salts can be prepared by a conventional two-step process, comprising the steps of (a) reacting a tertiary phosphine with an alkylhalide to obtain a quaternary phosphonium halide salt, and (b) exchanging the halide anion with a suitable anion (by ion exchange or metathesis) to generate a quaternary phosphonium salt having a non-halide anion.

However, this two-step process has several drawbacks. For example, the alkylhalides used to quaternize the tertiary phosphine are expensive and some are corrosive and difficult to prepare and use. Also, the tertiary phosphine may be expensive or difficult to make, the preparation thereof sometimes involving several steps and starting materials that are expensive and pyrophoric (see for example Kanazawa et al., supra, and Hugh R. Hays, *J. Org. Chem.* Vol. 31, pp. 3871-3820, which describe methods for preparing trimethylalkylphosphonium halides).

In addition, the two-step process generates large amounts of waste, as salt or acid by-products are usually removed by washing with water. Thus, the two-step process is inconvenient on an industrial scale.

Further, the end-product of the two-step process can be contaminated with residual halide ion, which may interfere with the intended utility of the phosphonium salt. For instance, halide ions such as chloride ions coordinate with group VII metals such as palladium and platinum and as a result, the presence of chloride ion can interfere with the activity of group VII metal catalysts. If a phosphonium salt is to be used in an environment where halide ions are unacceptable, even at low levels, halide salts should not be used in the starting materials or a further process must be used which ensures removal of halide ions from the phosphonium salt.

SUMMARY OF THE INVENTION

In one aspect, the present invention provides a method of preparing a phosphonium salt, the method comprising reacting a compound of formula I:

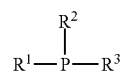
(I)

wherein $R^1$ is hydrogen, $R^2$ is hydrogen or hydrocarbyl, and $R^3$ is hydrocarbyl, with an ester compound defined by:

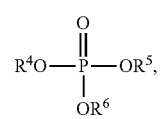
(II)

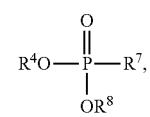
(III)

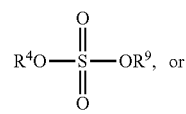
(IV)

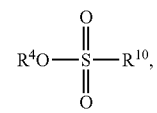
(V)

wherein each of $R^4$, $R^5$, $R^6$, $R^7$, $R^8$, $R^9$, and $R^{10}$ is independently hydrocarbyl, to form a phosphonium salt of formula VII:

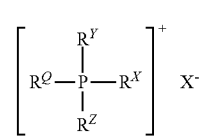
(VII)

wherein $R^Q$ is selected from $R^4$ and $R^2$ when $R^2$ is hydrocarbyl, $R^X$ is selected from $R^4$ and $R^3$, each of $R^Y$ and $R^Z$ is independently $R^4$, and $X^-$ is

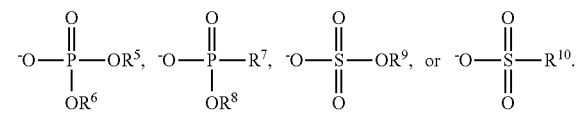

Some of the compounds of formula VII that can be prepared by the foregoing process are novel. Thus, in another aspect, the invention provides a compound of formula VII:

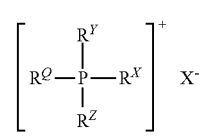
(VII)

wherein each of $R^Q$, $R^X$, $R^Y$, and $R^Z$ is independently hydrocarbyl; and $X^-$ is

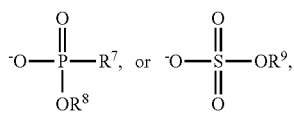

wherein each of $R^7$, $R^8$, and $R^9$ is defined as above, with the provisos that:

when $X^-$ is a phosphonate anion, then $R^Q$, $R^X$, $R^Y$, and $R^Z$ each has three or more carbon atoms;

when $X^-$ is a sulfate then the sum of carbon atoms in $R^Q$, $R^X$, $R^Y$, and $R^Z$ is greater than 4; and when $X^-$ is methylsulfate, and one of $R^Q$, $R^X$, $R^Y$, and $R^Z$ is methyl, the other of $R^Q$, $R^X$, $R^Y$, and $R^Z$ cannot all be 2-cyanoethyl.

DETAILED DESCRIPTION OF THE INVENTION

Figure 1:
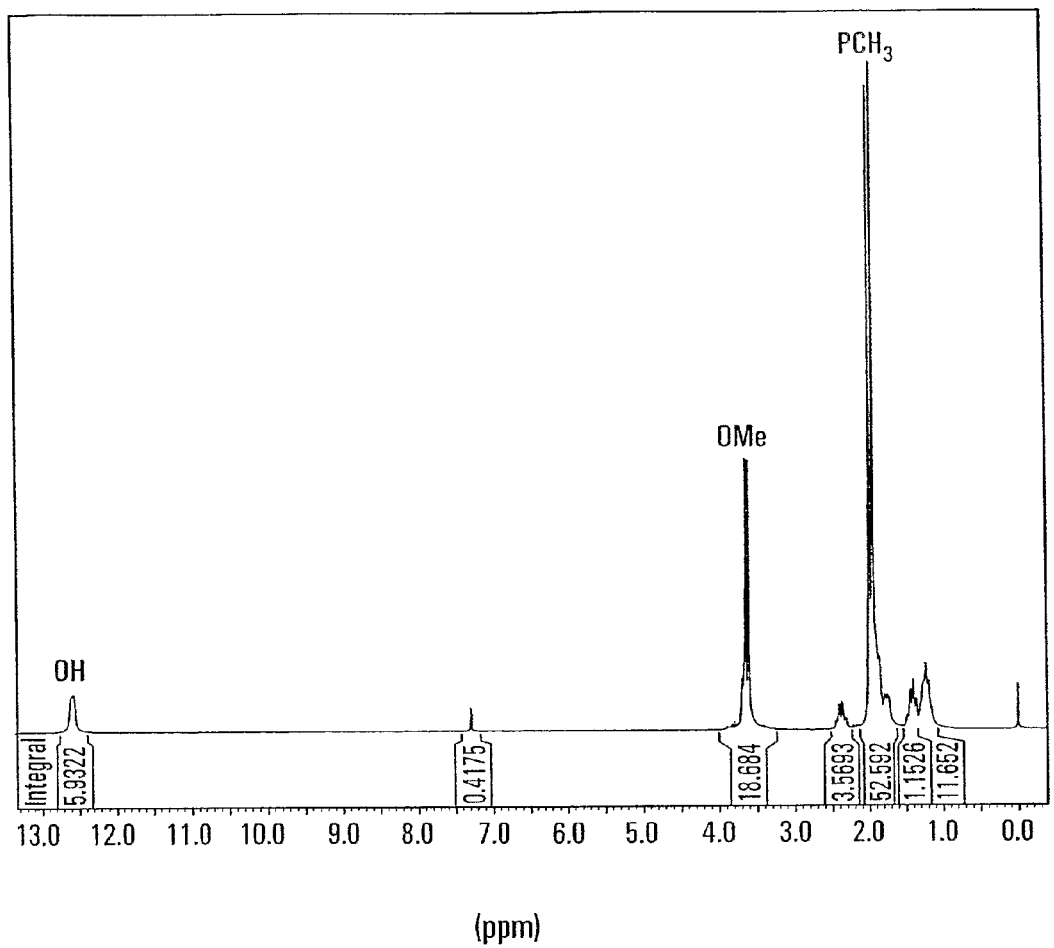
FIG. 1 is a $^1$H-NMR (proton nuclear magnetic resonance) spectrum of a mixture of cyclohexyltrimethylphosphonium dimethylphosphate and dimethylphosphoric acid.

In general, a phosphonium salt of formula VII can be prepared by reacting a phosphine of formula I (hereinafter referred to as the "starting phosphine") with an ester compound selected from the group consisting of: a phosphate triester of formula II; a phosphonate diester of formula III; a sulfate diester of formula IV; and a sulfonate ester of formula V. The overall reaction generates a quaternary phosphonium salt of formula VII and an acid counterpart of the ester (i.e. phosphoric acid, phosphonic acid, sulfuric acid, or sulfonic acid, respectively).

In one embodiment, the current method may be used for preparing a phosphonium of formula VII that has one or more methyl groups (i.e. one, two, three, or four methyl groups) attached to the phosphorus atom.

The current method may be especially suitable for preparing compounds of formula VII that are substantially free of halide ions.

In general, when the starting phosphine is a primary phosphine or a secondary phosphine, the ester is present in about three-fold or two-fold molar excess, respectively, relative to the starting phosphine, so as to provide roughly stoichiometric amounts of reagents. Specifically, when the starting phosphine is a primary phosphine (i.e. has a one hydrocarbyl group and two hydrogens attached to the phosphorus atom), the ester is present in about 3-fold molar excess of ester relative to starting phosphine. When the starting phosphine is a secondary phosphine (i.e. has two hydrocarbyl groups and one hydrogen attached to the phosphorus atom), the ester is present in about 2-fold molar excess of ester relative to starting phosphine. However in some cases, yields may be improved by using an excess of ester, for example in the range of about 1.05 to about 3.0 fold excess relative to the stoichiometry of the overall reaction and preferably about 1.1 to about 1.2 fold excess relative to the stoichiometric amount.

The temperature of the reaction is not critical and may range from about room temperature to about 260° C. or higher, although lower temperatures will result in longer reaction times. In general, the reaction proceeds readily at elevated temperature, say between about 80° C. to about 220° C., preferably in the range of 100-190° C., and is often complete in 8 hours at these temperatures.

However, as $R^4$ groups on the ester increase in size (i.e. steric bulk), the reaction may become less efficient and higher temperatures or longer reaction times may be necessary to increase yield. Therefore, suitable values for $R^4$ include but are not limited to: methyl, ethyl, n-propyl, isopropyl, n-butyl, iso-butyl, and tert-butyl. Certain esters, such as dimethylsulfate, are very active alkylating reagents and may be used for reactions carried out at moderate temperatures.

Also, the properties of the starting phosphine may affect the overall rate of the reaction. Secondary phosphines tend to be more reactive than primary phosphines. Thus, in general, reactions involving primary phosphine are carried out at higher temperatures or for longer times or both than are counterpart reactions involving secondary phosphines.

The starting phosphine can be added directly to an ester (a phosphate triester, a phosphonate diester, a sulfate diester, or a sulfonate ester), with stirring. However, the overall reaction is exothermic. Therefore, in order to control the temperature of the reaction mixture, it may be desirable to control the rate of addition in some cases and perhaps also to apply external cooling during the addition step. In addition, since alkylphosphines may be pyrophoric, it may be desirable to control the rate of addition of mono- or di-alkylphosphine so as to avoid having a large amount of unreacted mono- or di-alkylphosphine present in the reaction mixture, especially when the reaction is being carried out at elevated temperatures, for example over 100° C.

When the starting phosphine is a liquid at the temperature to be used for carrying out the reaction, the pressure of the reaction is not critical, and the reaction may be conveniently carried out at atmospheric pressure, under an inert atmosphere, such as nitrogen. Some primary and secondary phosphines that have short chain alkyl groups (such as dimethylphosphine) have low boiling points and may be gaseous and the temperature to be used for carrying out the reaction. When the starting phosphine is a gas at the temperature to be used for carrying out the reaction, the reaction is suitably carried out under pressure (e.g. in an autoclave) under an inert atmosphere, such as nitrogen.

The reaction can be carried out in the absence of solvent, in order to avoid a further step of purifying product away from solvent. However, the reaction may also be carried out in the presence of a solvent. In some cases, the presence of a solvent may be preferred as the solvent may enhance the rate at which the reaction proceeds.

If desired, any unreacted starting materials may be removed, for example, by evaporating under vacuum.

The method of the invention produces a mixture of phosphonium salt and acid which may be used directly, for example as a solvent for chemical reactions. Alternatively, the mixture of phosphonium salt and acid may be subjected to purification steps to isolate the phosphonium salt. For example, dimethylphosphoric acid and methyl hydrogen sulfate can be removed from the reaction mixture by evaporation, for example under vacuum at elevated temperatures (dimethylphosphoric acid decomposes at 172-176° C., and methyl hydrogen sulfate decomposes at 130-140° C.; see *Handbook of Chemistry and Physics*, 57$^{th}$ Edition, CRC Press, Inc., copyright 1976, pages C-435 and C-508). Alternatively, the acid product can be removed by neutralizing the acid with a hydroxide of a Group II metal (i.e. an alkaline earth metal hydroxide, such as calcium hydroxide or barium hydroxide) to form a precipitate and recovering the precipitate by suitable means, such as filtration. Of note, calcium dimethylphosphate, a chemical that finds utility in polyester fibre processing (JP2001164461), can be prepared by the foregoing process. If the phosphonium salt forms a two-phase system when mixed with water, it may be possible to remove acid by washing the phosphonium salt with water. Other purification processes known in the art, such as chromatography, can also be used to purify the phosphonium salt from the reaction mixture.

Suitable hydrocarbyl groups for $R^Q, R^X, R^Y, R^Z, R^2, R^3, R^4, R^5, R^6, R^7, R^8, R^9$, and $R^{10}$ include: substituted or unsubstituted $C_1$-$C_{30}$ alkyl, substituted or unsubstituted $C_3$-$C_8$ cycloalkyl, substituted or unsubstituted $C_2$-$C_{30}$ alkenyl, substituted or unsubstituted $C_2$-$C_{30}$ alkynyl, substituted or unsubstituted $C_6$-$C_{18}$ aryl, or substituted or unsubstituted $C_7$-$C_{35}$ aralkyl, although hydrocarbyl groups with not more than 20 carbon atoms are preferred. $R^2$ and $R^3$ together with the phosphorus atom to which $R^2$ and $R^3$ are bonded can form a five- to eight-membered heterocycle or a heterobicycle, such as 9-phosphabicyclo[3.3.1]nonane. It is noted that $R^2$ and $R^3$ can be perfluoroalkyl. It is possible for the R groups ($R^Q, R^X, R^Y, R^Z, R^2$ and $R^3$ when not perfluoroalkyl and $R^4$ to $R^{10}$) to bear substituents, or to include heteroatoms, provided that the substituents or heteroatoms do not interfere with the preparation of the compounds of the invention, and do not adversely affect the desired properties of the compound. Acceptable substituents may include alkoxy, halo, carboxy, and acetyl, and heteroatoms that may be acceptable include nitrogen, oxygen and sulphur. Substituents are likely to increase the cost of the compounds of the invention and as the compounds are often used in industrial applications (as solvents, surfactants, etc.), they are used in such volume that cost is a significant factor. Hence, it is contemplated that, for the most part, substituents will not be present, except for compounds in which one or more of $R^2$ and $R^3$ is perfluoroalkyl. If necessary, one of skill in the art can readily determine whether substituents or heteratoms of the hydrocarbyl groups interfere with preparation or desired properties of the compounds by routine experimentation that does not involve the exercise of any inventive faculty.

In many cases, $R^Q, R^X, R^Y, R^Z, R^2, R^3, R^4, R^5, R^6, R^7, R^8, R^9$, and $R^{10}$ will be substituted or unsubstituted alkyl groups of 1 to 20 carbon atoms. Thus, specific examples of values for $R^Q, R^X, R^Y, R^Z, R^2, R^3, R^4, R^5, R^6, R^7, R^8, R^9$, and $R^{10}$ include: methyl, ethyl, n-propyl, isopropyl, n-butyl, iso-butyl, tert-butyl, n-pentyl, cyclopentyl, iso-pentyl, n-hexyl, cyclohexyl, norbornyl, 3-methylphenyl (2,4,4'-trimethyl)pentyl, cyclooctyl, tetradecyl, etc. $R^2$ and $R^3$ can also be trifluoromethyl.

Mention is made of the following examples of values for $R^2$ and $R^3$: methyl, trifluoromethyl, ethyl, n-propyl, iso-propyl, n-butyl, iso-butyl, tert-butyl, cyclopentyl, cyclohexyl, and norbornyl, and the case where $R^2$ and $R^3$ together with the phosphorus atom to $R^2$ and $R^3$ are bonded form 9-phosphabicyclo[3.3.1]nonyl.

Mention is made of the following examples of values for $R^4, R^5, R^6, R^7, R^8, R^9$, and $R^{10}$: methyl, ethyl, n-propyl, isopropyl, n-butyl, iso-butyl, and tert-butyl. It is noted that $R^{10}$ can also be p-toluenyl. Examples of suitable esters for use in the inventive method include but are not limited to: trimethylphosphate, dimethylsulfate, dimethylmethanephosphonate, and methyltosylate.

Phosphonium cations in which $R^Q, R^X, R^Y$, and $R^Z$ are not identical are referred to as "asymmetric". In some cases, it is desired that $R^Q, R^X, R^Y$, and $R^Z$ shall not be identical and in particular, that at least one of $R^Q, R^X, R^Y$, and $R^Z$ shall contain a significantly higher number of carbon atoms (for example 14 to 20 carbon atoms) than the others of $R^Q, R^X, R^Y$, and $R^Z$.

For some applications, it is desired that at least one of $R^Q, R^X, R^Y$, and $R^Z$ shall contain a low number of carbon atoms (for example 1 to 3 carbon atoms, more preferably 2 carbon atoms, and even more preferably one carbon atom). For example, one, two, three or all of $R^Q, R^X, R^Y$, and $R^Z$ can be methyl. Phosphonium salts with a low carbon content, say between 5 to 12 carbon atoms, may find utility as ionic liquids or electrolytes in cases where a high ratio of charge to molecular weight is required.

Phosphonium salts that may be used as surfactants include those in which three of $R^Q, R^X, R^Y$, and $R^Z$ are each independently methyl or ethyl, preferably methyl, and the other is a saturated hydrocarbyl having an unbranched chain of a higher number of carbon atoms, say 12 to 30 carbon atoms, more preferably 12 to 20 carbon atoms. By a "surfactant" we mean a surface-active agent that reduces surface tension when dissolved in water or water solutions, or that reduces interfacial tension between two liquids, or between a liquid and a solid. Surfactants include detergents, wetting agents, and emulsifiers. Surfactants may form micelles. The hydrocarbyl chain on the phosphonium may bear substituents that do interfere with intended utility of the compound as a surfactant, including but not limited to fluoro.

In some cases, it is preferred that at least one of $R^Q, R^X, R^Y, R^Z$ or $R^5$ to $R^{10}$ contains a higher number of carbon atoms, for example 14 or more. For example, the presence of one or more long alkyl chains may increase the ability of a phosphonium salt to dissolve nonpolar organic compounds. In addition, the presence of one or more long alkyl chains may render the phosphonium salt "water immiscible".

Compounds according to formula VII that are hydrophobic or "water immiscible" are preferred for some purposes. The term "water immiscible" is intended to describe compounds that form a two phase system when mixed with water but does not exclude compounds that dissolve in water nor compounds that will dissolve water, provided that the two phase system forms. Water immiscibility is a desirable feature of a phosphonium salt not only because it renders the compound useful as a solvent for biphasic reactions with an aqueous phase, but also because it facilitates purification and isolation of the phosphonium salt when prepared according to certain methods. By way of illustration, when the method of the invention produces a water-immiscible phosphonium salt and an acid, the acid can be removed from the reaction products by washing the phosphonium salt with water. Compounds of formula VII that have a large total number of carbons, say equal to or greater than 20 and in particular greater than 25 or 26, or have at least one aryl group are more hydrophobic. There is no critical upper limit on the total number of carbon atoms that may be present in a compound of formula VII. However, it is unlikely that the total will exceed 50.

If the compound of formula VII is intended for use as a solvent, then in general, it is preferred that the compound is a liquid below 100° C., more preferably below 50° C., and most preferably at or below room temperature. Values for $R^Q, R^X, R^Y, R^Z, R^2, R^3, R^4, R^5, R^6, R^7, R^8, R^9$, and $R^{10}$ can be selected to yield compounds that are liquid at room temperature. Increasing the total number of carbon atoms present in the hydrocarbyl groups $R^Q, R^X, R^Y, R^Z$, and $R^2$ to $R^{10}$ will tend to increase the melting point, although this effect can be counteracted somewhat by asymmetry, branching of the hydrocarbyl groups $R^Q, R^X, R^Y, R^Z$, and $R^2$ to $R^{10}$, and the tendency of sterically bulky ions to coordinate poorly. Specifically, the melting point tends to decrease as the degree of asymmetry around the phosphorus atom increases. Also, the melting point of the salt will tend to decrease as the degree of branching of the hydrocarbyl groups $R^Q$, $R^X$, $R^Y$, $R^Z$, and $R^2$ to $R^{10}$ increases. Branching can occur at the alpha or omega carbon or at any intermediate point. In addition, the melting point of the salt will tend to decrease as steric bulk increases around either or both of the phosphorus atom of the cation and the central atom of the anion (the sulfur atom or phosphorus atom or carbon atom); for this reason, it may be preferred for one or more of R groups on either or both of the cation and anion (i.e. $R^Q$, $R^X$, $R^Y$, $R^Z$, $R^5$, $R^6$, $R^7$, $R^8$, $R^9$, and $R^{10}$) to have three or more carbon atoms.

Thus, the current invention contemplates compounds of formula VII where properties may be modified by varying the values of the R groups present on either the anion or the cation. Selection of particular values for $R^Q$, $R^X$, $R^Y$, $R^Z$, and $R^2$ to $R^{10}$ to achieve particular melting points, degrees of water immiscibility, or surfactant properties is within the competence of a person skilled in the art, although it may require some routine experimentation.

Compounds according to formula VII that have chirality provide a chiral environment for chemical reactions and may be especially suitable for certain purposes, such as a reaction having an asymmetric or chiral transition state that can be stabilized by interaction with a suitable solvent. Examples of chiral compounds of formula VII include compounds containing a phosphonium cation wherein $R^Q$, $R^X$, $R^Y$, and $R^Z$ are all different or wherein one of $R^Q$, $R^X$, $R^Y$, and $R^Z$, is an enantiomer, such as 2,4,4'-trimethylpentyl, which group has one chiral atom.

Mention is made of the following examples of compounds of formula VII:
cyclohexyltrimethylphosphonium dimethylphosphate;
dibutyldimethylphosphonium dimethylphosphate;
dicyclohexyldimethylphosphonium dimethylphosphate; and
diisobutyldimethylphosphonium dimethylphosphate.

Phosphonium salts described herein may find utility in a wide range of applications. For example, phosphonium salts in which three of $R^Q$, $R^X$, $R^Y$, and $R^Z$ are methyl and the other is a saturated or unsaturated hydrocarbyl having an unbranched chain of a higher number of carbon atoms, say 12 to 30 carbon atoms, may find utility as antimicrobial agents (Kanazawa, supra) or surfactants. Phosphonium phosphates may find utility as a component of spinning finish (JP11172577). The phosphonium salts of the current invention may also be used as polar solvents known as "ionic liquids" for chemical reactions such as Michael additions, aryl coupling, Diels-Alder, alkylation, biphasic catalysis, Heck reactions, hydrogenation, or for enzymatic reactions, for example lipase reactions (for a recent review of ionic liquids, see Thomas Welton (Chem. Rev. 1999, 99, 2071-2083)).

EXAMPLES

In the following examples, starting material phosphines are made by Cytec Canada, Inc. and their purity determined by gas chromatography (GC). The remaining starting materials were purchased from Aldrich and used as they were purchased. Structures were confirmed by NMR (nuclear magnetic resonance spectrometry) and by FAB MS (Fast Atom Bombardment mass spectrometry), as indicated.

Example 1

Preparation of Cyclohexyltrimethylphosphonium Dimethylphosphate

Cyclohexylphosphine (14.5 g, 98%, 0.1255 mole) was added by dripping through an addition funnel over a period of 10 minutes to a flask containing trimethylphosphate (95 g, 97%, 0.6578 mole, b.p. 197° C.) preheated to 140° C. under nitrogen, with stirring. There was no sudden change in temperature associated with addition. The mixture was heated to reflux (about 165° C.).

As the reaction proceeded, the temperature of the mixture gradually increased to 210° C. and was maintained at this temperature with stirring for 15 minutes. The total reaction time was about 8 hours.

The reaction mixture was then cooled and decanted into a flask. Excess trimethylphosphate was removed from the reaction mixture by heating to 180° C. under vacuum 5 mm Hg.

Figure 2:
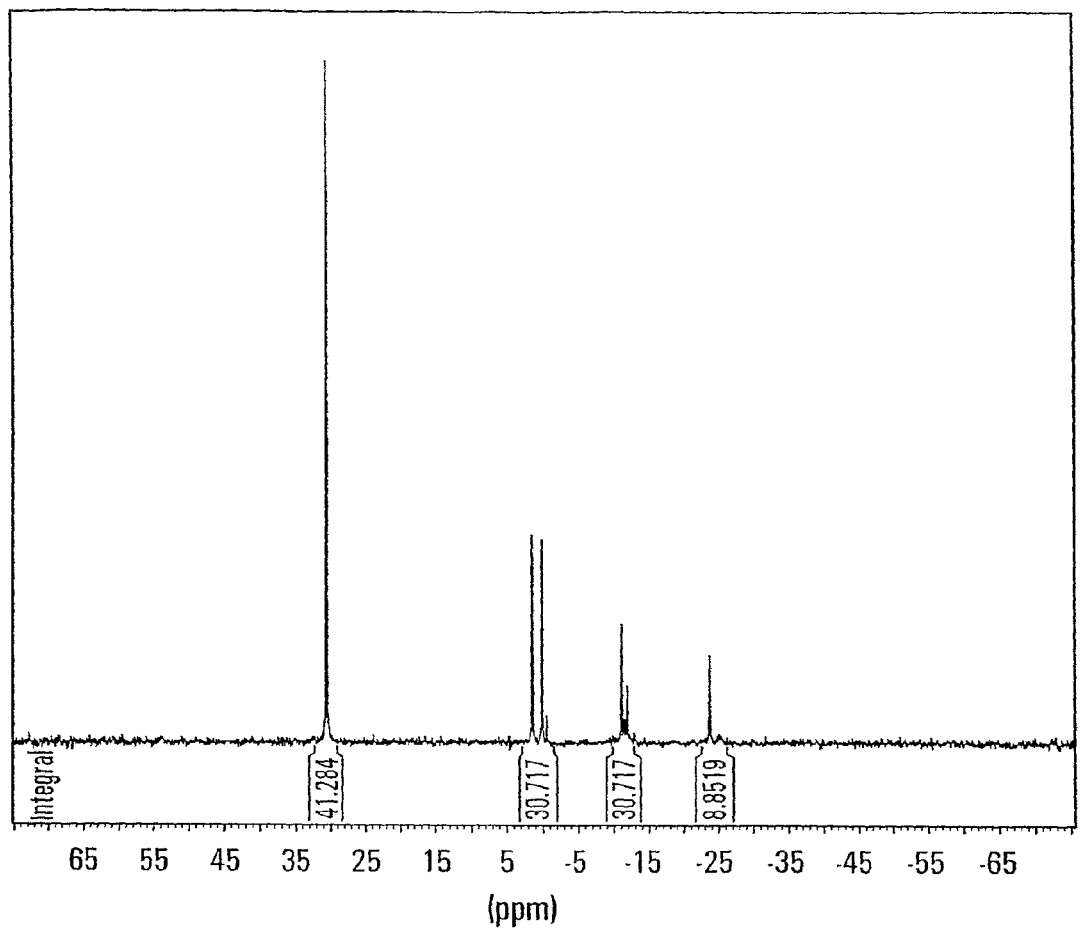
FIG. 2 is a $^{31}$P-NMR of a mixture of cyclohexyltrimethylphosphonium dimethylphosphate and dimethylphosphoric acid.

The product was a glassy, colourless liquid with a pH of about 2-3 pH units. The presence of cyclohexyltrimethylphosphonium dimethylphosphate and dimethylphosphoric acid was confirmed by $^1$H (see FIG. 1), $^{13}$C, and $^{31}$P (see FIG. 2) NMR and FAB MS analysis. $^1$H-NMR (CDCl$_3$, 300.13 Hz, δ) signals for the characteristic methyl groups are: 1.96 (d, J=14.2 Hz, P—CH$_3$), 3.62 (d, J=10.8 Hz, O═P—O—CH$_3$); $^{31}$P-NMR (CDCl$_3$, 81.015 Hz, δ): 30.60 (P$^+$), 1.63 (O═P—O—CH$_3$).

Example 2

Preparation of Dibutyldimethylphosphonium Dimethylphosphate

A 500 ml 2 neck round-bottomed flask fitted with a condenser was charged with 108.0 g (0.77 mole) trimethylphosphate and heated to 135° C. under nitrogen with stirring. Di-n-butylphosphine (93.2 g, 0.64 mole) was added to the flask over a period of 8 hours. The temperature of the contents of the flask increased to 155° C. during the addition of a first 6.6 g of the total 93.2 g of di-n-butylphosphine. The reaction was maintained at 150° C. for 2 hours.

Following the incubation period, unreacted trimethylphosphate was removed by evaporation for 6 hours at 100° C. under reduced pressure (20 mmHg).

A colourless and viscous liquid (180.7 g) was obtained. $^{31}$P, $^{13}$C and $^1$H NMR and FAB MS confirmed the presence of dibutylphosphonium dimethylphosphate and dimethylphosphoric acid. $^1$H-NMR (CDCl$_3$, 300.13 Hz, δ) signals for the characteristic methyl groups are: 1.65 (d, J=13.8 Hz, P—CH$_3$), 3.20 (d, J=10.6 Hz, O═P—O—CH$_3$); $^{31}$P-NMR (CDCl$_3$, 81.015 Hz, δ): 30.36 (P$^+$), 2.06 (O═P—O—CH$_3$).

Example 3

Preparation of Dicyclohexyldimethylphosphonium Dimethylphosphate

A round-bottomed flask fitted with a condenser was charged with 280.3 g (1.9 mole) trimethylphosphate and heated to 100° C. under nitrogen with stirring. Dicyclohexylphosphine (277.2 g, 1.4 mol) was gradually added to the flask over a period of 7.5 hour. The reaction was exothermic, with the temperature of the contents of the flask rising rapidly to 150-160° C. during the addition of dicyclohexylphosphine. The reaction mixture was maintained at a temperature of 150-160° C. for 2 hours, then cooled to room temperature.

Upon cooling to room temperature, the product crystallized into a clear, colourless solid. Unreacted trimethylphosphate was removed by evaporation under reduced pressure (5 mmHg) at 170° C. for 12 hour.

Analysis by $^{31}$P and $^1$H NMR and MS confirmed the presence of dicyclohexyldimethylphosphonium dimethylphosphate and dimethylphosphoric acid. $^1$H-NMR (CDCl$_3$, 300.13 Hz, δ) signals for the characteristic methyl groups are: 1.76 (d, J=13. Hz, P—CH$_3$), 3.39 (d, J=10.6 Hz, O=P—O—CH$_3$); $^{31}$P-NMR (CDCl$_3$, 81.015 Hz, δ): 34.48 (P$^+$), 2.28 (O=P—O—CH$_3$).

Example 4

Preparation of Diisobutyldimethylphosphonium Dimethylphosphate

A round-bottomed flask was charged with 136.0 g (0.96 mole) trimethylphosphate and heated to 140° C. under nitrogen with stirring. While stirring vigorously, a solution of 70.3 g (0.48 mol) diisobutylphosphonium and 11.0 g of dimethylcarbonate were added to the flask over a period of 2.5 hours at 135° C. The reaction was exothermic during the addition of the phosphine. The reaction mixture was maintained at 135° C. for a total of 8 hours, then cooled room temperature. $^{31}$P, $^1$H, and $^{13}$C NMR analyses confirmed the presence of the diisobutyldimethylphosphonium dimethylphosphate and dimethylphosphoric acid.

We claim:

1. A method of preparing a phosphonium salt, the method comprising:

reacting a compound of formula I:

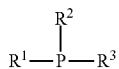
(I)

wherein R$^1$ is hydrogen, R$^2$ is hydrogen or hydrocarbyl, and R$^3$ is hydrocarbyl, with an ester compound defined by:

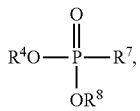
(III)

wherein each of R$^4$, R$^7$ and R$^8$ is independently hydrocarbyl, to form a phosphonium salt of formula VII:

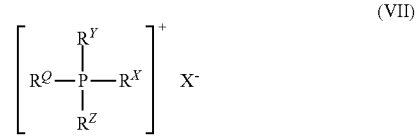
(VII)

wherein R$^Q$ is selected from R$^4$ and R$^2$ when R$^2$ is hydrocarbyl, R$^X$ is selected from R$^4$ and R$^3$, each of R$^Y$ and R$^Z$ is independently R$^4$, and X$^-$ is

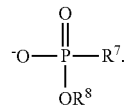

2. The method of claim 1, wherein R$^2$ is hydrogen and R$^3$ is a hydrocarbyl.

3. The method of claim 1, wherein each of R$^2$ and R$^3$ are both hydrocarbyl.

4. The method of claim 1, wherein the hydrocarbyl is a substituted or unsubstituted alkyl group of 1 to 20 carbon atoms.

5. The method of claim 4, wherein the hydrocarbyl is selected from the group consisting of: methyl, trifluoromethyl, ethyl, n-propyl, iso-propyl, n-butyl, iso-butyl, tert-butyl, cyclopentyl, cyclohexyl, and norbornyl.

6. The method of claim 3, wherein R$^2$ and R$^3$ together with the phosphorus atom to which R$^2$ and R$^3$ are bonded form a five- to eight-membered heterocycle or heterobicycle.

7. The method of claim 6, wherein the heterobicycle is 9-phosphabicyclo[3.3.1]nonyl.

8. The method of claim 1, wherein R$^4$ is selected from the group consisting of: methyl, ethyl, n-propyl, iso-propyl, n-butyl, iso-butyl, and tert-butyl.

9. The method of claim 8, wherein R$^4$ is methyl.

10. The method of claim 1, wherein the phosphonium salt has a total number of carbon atoms between 20 and 50.

11. The method of claim 10, wherein the phosphonium salt has a total number of carbon atoms between 25 and 50.

12. The method of claim 1, wherein the phosphonium salt is water immiscible.

13. The method of claim 1, wherein the phosphonate ester is dimethylmethanephosphonate.

* * * * *